United States Patent [19]

Citterio et al.

[11] Patent Number: 4,608,441

[45] Date of Patent: Aug. 26, 1986

[54] PROCESS FOR THE PREPARATION OF ARYLALKANOIC ACIDS BY OXIDATIVE REARRANGEMENT OF ARYLALKANONES

[75] Inventors: Attilio Citterio, Monza; Laura Tinucci, San Giuliano Milanese; Aldo Belli, Cornate d'Adda; Lucio Filippini, Saronno, all of Italy

[73] Assignee: BLASCHIM S.p.A., Milan, Italy

[21] Appl. No.: 754,538

[22] Filed: Jul. 12, 1985

[30] Foreign Application Priority Data

Jul. 13, 1984 [IT] Italy ................................. 21803 A/84

[51] Int. Cl.[4] ..................... C07C 65/11; C07D 333/24
[52] U.S. Cl. .................................. 562/466; 562/469; 562/465; 562/496; 549/79
[58] Field of Search ....................... 562/466, 465, 496; 549/79

[56] References Cited

U.S. PATENT DOCUMENTS

| 4,535,166 | 8/1985 | Castaldi | 562/496 |
| 4,542,237 | 9/1985 | Schloemer | 562/496 |

FOREIGN PATENT DOCUMENTS

| 64394 | 11/1982 | European Pat. Off. | 562/496 |
| 151817 | 8/1985 | European Pat. Off. | 562/496 |
| 153701 | 9/1985 | European Pat. Off. | 562/496 |
| 154853 | 9/1985 | European Pat. Off. | 562/496 |

*Primary Examiner*—Paul J. Killos
*Attorney, Agent, or Firm*—Berman, Aisenberg & Platt

[57] ABSTRACT

Process for preparing an arylalkanoic acid by adding iodine to a mixture of an arylalkanone and an excess of an orthoester, heating of the mixture thus obtained, adding an inorganic base and finally an acid.

16 Claims, No Drawings

PROCESS FOR THE PREPARATION OF ARYLALKANOIC ACIDS BY OXIDATIVE REARRANGEMENT OF ARYLALKANONES

This invention relates to a process for preparing an arylalkanoic acid which comprises the addition of iodine to a mixture of an arylalkanone and an excess of an orthoester, heating of the reaction mixture, the addition of an inorganic base and finally of an acid.

More particularly, this invention relates to the preparation of an arylalkanoic acid according to the following reaction diagram:

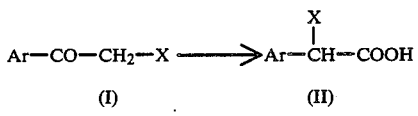

wherein X is H or a $C_1$–$C_4$ alkyl radical, and Ar is selected from the group comprising an aryl, a substituted aryl, a fused heterocyclic aryl, a heterocycle, a substituted heterocycle and a fused aryl heterocycle radical.

It is known that many arylalkanoic acids are useful as drugs and others as intermediates. More particularly many members of this class are known to be useful as anti-inflammatory, analgesic, and antipyretic agents. Examples of these compounds include Thiaprofenic acid, Ibuprofen, Fenclorac, Indoprofen, Flurbiprofen, Naproxen, Ketoprofen, Fenoprofen, Piroprofen, Suprofen, Aclofenac, Xenbucin, Diclofenac and Tolmetin (Anti-inflammatory Drugs, Springer Verlag, 1979, pages 321–3) and Isoprofen, FLP-58,302 (CAS-58282-60-3-), Furofenac, Cicloprofen, Y-8004 (Drugs of the Future 2, 217 (1977)), Caroprofen, Benoxaprofen, Y-9213 (Drugs of the Future 4, 373, 1978), Enprofen, Benzofenac, Fenclofenac, Isoxepac, Oxepinal, Tiopinac, Zomepirac, and Fentiazac.

Because of the great interest assumed by arylalkanoic acids in recent years, research has been intensified to find a preparation method which would make it possible to manufacture the acids of Formula II starting from inexpensive compounds such as the ketones of Formula I, in a single vessel and without isolating and purifying intermediate products, if any.

A first attempt is the one described in U.S. Pat. Nos. 4,107,439, 4,135,051 and 4,412,054, which requires the use of trivalent thallium nitrate. This process suffers from many draw-backs, but the main one is that it gives rise to highly toxic by-products which do not allow the use of arylalkanoic acids thus prepared as pharmaceuticals.

S. D. Higgins and C. B. Thomas (J. C. S. Perkin Trans, 1982, 235–42; idem, 1983, 1483–88) put forward various hypotheses about the mechanism of said reaction for the purpose of replacing thallium nitrate with nontoxic and more economical reagents and, to check the correctness of their hypotheses, they tested various oxidizing systems; the best yields are given by the system consisting of iodine, silver nitrate, trimethylorthoformate and methanol, but the authors themselves acknowledge that the large quantity of silver nitrate required makes this process uneconomical (ibid, 1982, 239) and that the reaction does not proceed at all in the absence of silver nitrate (ibid, 1983, 1483).

In European Patent Application No. 108,442 a method is described according to which the silver nitrate is substituted by zinc chloride, but the yields obtained with this method are rather small.

It has now been found that the system described by S. D. Higgins et al. affords excellent yields even in the absence of silver nitrate and methanol, provided a substantial excess of alkylorthoformate or other orthoesters are used.

This invention relates to a process for preparing an arylalkanoic acid of Formula II which comprises the addition of iodine to a mixture of an arylalkanone of Formula (I) and an excess of an orthoester, heating of the mixture thus obtained, the addition of an inorganic base, and finally the addition of an acid.

To the reaction mixture may be added a suitable solvent, a diluent and/or a catalytic quantity of a protic acid.

The iodine is added in the amount of approximately 1.05 mole for each mole of arylalkanone. The quantity of iodine used may be substantially reduced by adding a suitable oxidant which restores the iodine from the hydriodic acid which is formed in the course of the reaction. It has been also noted that the presence of a peroxide plays an important role in the kinetics of the process which, for the more reactive systems, is expressed with a considerable reduction in reaction times while in less reactive systems or those which interact with hydriodic acid it is expressed by appreciable increases in yields. Examples of suitable oxidants are hydrogen peroxide, the organic peroxides, preferably the diacylperoxides, such as dibenzoyl or dodecanoyl peroxide, the peracids, such as m-chloroperbenzoic and permaleic acid, the peresters, such as tert-butyl-peracetate, tert-butylperbenzoate, di-tert-butylperoxalate, di-tert-butyl-perisobutyrate, and di-tert-butyl-cyclohexylpercarbonate and the hydroperoxides, such as tert-butylhydroperoxide and cumylhydroperoxide.

The orthoester is added in the amount of at least 2 moles for each mole of arylalkanone; the addition of quantities between 1 and 2 moles gives smaller yields while the addition of more than 10 moles does not give appreciable advantages.

Suitable orthoesters are the alkylorthoformates, the alkylorthoacetates and the alkylorthocarbonates in which the alkyl has from 1 to 10 carbon atoms and preferably from 1 to 4 carbon atoms.

The presence of a solvent, a diluent and/or a catalytic quantity of a protic acid is not strictly necessary.

The addition of a solvent or a diluent is nevertheless useful when the arylalkanone is not very soluble in the orthoester or when it is not very reactive at the boiling temperature of the orthoester.

Examples of solvents which increase the solubility of the arylalkanone in the reaction mixture are the aliphatic alcohols and glycols with 1–10 carbon atoms. Selection of the aliphatic alcohol and orthoester will preferably be made in such a way that the alcohol corresponds to that used as a precursor of the orthoester. When a glycol is used, it is preferable to operate in the presence of the corresponding orthocarbonate.

When the arylalkanone reacts slowly at the boiling temperature of the orthoester, it will be preferable to add an inert organic diluent having a high boiling point, such as benzene, toluene, xylene and nitrobenzene.

The addition of a protic acid is also useful to bring the arylalkanone into solution.

Examples of suitable protic acids are hydrochloric, sulfuric, p-toluenesulfonic and methanesulfonic acid.

According to this invention a mixture of an arylalkanone and an orthoester and, optionally, a solvent, a diluent and/or a protic acid is refluxed until it becomes clear. This occurs in between 5 minutes and 24 hours. Iodine is the added at a temperature between room temperature and the boiling temperature of the reaction mixture and, when the quantity of iodine is less than 1.05 mole for each mole of arylalkanone, an oxidant is also added.

The reaction mixture is then again heated to reflux until a sample of the reaction mixture reveals the presence of the keto group when treated with an aqueous solution of 5% hydrochloric acid. The time required for the keto group to disappear varies with the reactivity of the arylalkanone and the boiling temperature of the reaction mixture and can thus vary between one-half hour and 170 hours.

When the reaction is over, the excess iodine is destroyed by adding a reducing agent, such as sodium sulfite, sodium hydrosulfite and sodium thiosulfate and an inorganic base is added.

Examples of suitable inorganic bases are sodium hydroxide and potassium hydroxide.

The mixture thus obtained is again heated to boiling for from 30 minutes to six hours. Water is added, the mixture is acidified and the desired arylalkanoic acid is isolated with high yields. Said isolation is performed with the usual techniques, such as filtration, extraction with solvents, or fractional distillation.

The above process is carried out in a single vessel without isolating any intermediate product.

The iodine may be recovered in the form of alkyl iodide by distillation or in the form of iodine by oxidation of the mother liquors, for example with chlorine or sodium hypochlorite.

The solvents and/or the diluents are also easily recoved by fractional distillation.

The process according to this invention thus makes it possible to prepare the arylalkanoic acids of Formula II in an extremely economical manner because high yields are obtained, because economical or in any case readily recovered raw materials are used, and because the process is carried out in a single vessel with no particular employment of labour.

The following examples illustrate the invention without limiting it.

EXAMPLE 1

Preparation of dl 2-(6'-methoxy-2'-naphthyl)-propionic acid:

(a) Iodine (136 g; 0.53 mole) was added to a solution of 1-(6'-methoxy-2'-naphthyl)-1-propanone (100 g; 0.47 mole), toluene (120 ml), methanol (4 g), and trimethylorthoformate (110 g; 1.04 mole) at 16° C. After 10 minutes the solution was heated to 26° C. and kept at this temperature for 1 hour. Trimethylorthoformate (100 g; 0.98 mole) was added and the mixture was heated to reflux (47° C.) for 22 hours.

The mixture was cooled and sodium sulfite (10 g), sodium hydroxide drops (20 g; 0.5 mole), and water (20 ml) were added and the mixture was heated to 60° C. for two hours. 5% hydrochloric acid (0.36 l) was added and the layers were decanted. The organic layer was dried and the solvent was removed by distillation.

Yield, 90%; m.p. 154°–155° C.

Similar results were obtained by substituting:
triethylorthoformate for the trimethylorthoformate (yield, 80%); and
nitrobenzene for the toluene (yield, 82%).

(b) To a solution of trimethylorthoformate (14.4 ml; 0.14 mole) in methanol (40 ml; 0.99 mole) was added 0.1 ml of a 48% solution of hydrochloric in methanol and the 1-(6'-methoxy-2'-naphthyl)-1-propanone (10 g; 0.047 mole). After 10 minutes the solution became homogeneous and was maintained under reflux for 2 hours. It was then cooled to 40° C. and iodine (11.85 g; 0.047 mole) was added. The reaction mixture was refluxed for 30 hours, the solvent was removed by distillation and the residue was treated with potassium hydroxide in methanol (0.20 mole in 40 ml) at boiling for 2 hours. The reaction mixture was evaporated to dryness, dissolved in water and extracted with ethyl ether. The aqueous layer was acidified to precipitate the dl 2-(6'-methoxy-2'-naphthyl)-propionic acid weighing (after drying) 8.65 g; m.p. 154°–155° C. (yield, 80%).

Similarly:
1-(6'-methoxy-5'-bromo-2'-naphthyl)-1-propanone (10 g; 0.034 mole) in methanol (34 ml), trimethylorthoformate (11.2 ml; 0.102 mole) and iodine (8,66 g) were preheated to reflux for 72 hours. Then the mixture was treated in a manner similar to that described above; yield, 80% of dl 2-(6'-methoxy-5'-bromo-2'-naphthyl)-1-propionic acid.

4-methoxy-propiophenone (5 g; 0.03 mole) in methanol (25 ml), trimethylorthoformate (10 ml; 0.09 mole), and iodine (7.62 g; 0.03 mole) were heated to reflux for 30 hours. Then the reaction mixture was treated in a manner similar to that described above; yield, 50% of 2-(4'-methoxyphenyl)-propionic acid, m.p. 57° C.

EXAMPLE 2

Preparation of 2-(2-thienyl)-propionic acid:

(a) Dibenzoylperoxide (25.5 g; 0.107 mole) and iodine (14.9; 0.0588 mole) were added to a solution of 2-propionylthiophen (15 g; 0.107 mole) in methanol (10 g) and trimethylorthoformate (40 g; 0.377 mole) containing hydrochloric acid gas (0.17 g) and maintained under stirring for 3 hours at 20° C. The mixture was allowed to stand at room temperature for 1 hour, then heated to 70° C. for 12 hours. After cooling to 30° C., sodium sulfite (5 g) and water (5 ml) were added and the reaction mixture was stirred for 30 minutes. Sodium hydroxide drops (8.8 g; 0.23 mole) were then added. The mixture was refluxed for 1 hour, acidified with 37% hydrochloric acid to pH 2–3, and extracted with ethyl ether. The extracts were dried, and the solvent and the product were distilled. 5.0 g of the desired product were obtained, b.p. 130° C. (3.5 mmHg); yield, 30%. This product is an useful intermediate for preparing Tiaprofenic acid.

Working in a similar manner, dl 2-(6'-methoxy-2'-naphthyl)-propionic acid was prepared by substituting the 2-propionylthiophen with 1-(6'-methoxy-2'-naphthyl)-propanone and the dibenzoylperoxide with:
laurylperoxide (reaction time: 12 h; reaction temperature: 50° C.); yield, 80%;
tert-butylperacetate (reaction time: 15 h; reaction temperature: 50° C.); yield, 91%;
tert-butylhydroperoxide (reaction time: 12 h; reaction temperature: 50° C.); yield, 70%;
(4-tert-butylcyclohexyl)-percarbonate (reaction time; 40 h; reaction temperature: 40° C.); yield, 85%.

(b) To a solution of 2-propionylthiophen (5 g; 35.7 mmole), methanol (5 g) and trimethylorthoformate (10 g; 94.2 mmole), were added dibenzoylperoxide (8.6 g; 35.7 mmole) and iodin (4.98 g; 19.6 mmole) portionwise in ½ hour. The mixture was heated to 40° C. for 4 hours and 60° C. for 15 hours. Then anhydrous sodium sulfite (1.5 g) and water (3 ml) were added, the mixture was stirred for ½ hour, sodium hydroxide (3.5 g; 88 mmole) was added and the mixture was refluxed for 2 hours. After distillation under reduced pressure at 50° C., the residue was taken up with water (100 ml) and the thus obtained mixture was extracted with methylene chloride (2×20 ml), discarding the organic solvent. The aqueous layer was acidified with 37% hydrochloric acid to pH 2–3 and extracted with methylene chloride (3×20 ml). The organic extracts were dried and the solvent was removed by distillation.

4.0 g of the desired product were obtained thus (titre, 97.5%); yield, 70%.

Working in a similar manner but substituting the 2-propionyltiophen with:

1-(6'-methoxy-2'-naphthyl)-propanone (reaction time: 17 hours; reaction temperature: 50° C.), the yield of 2-(6'-methoxy-2'-naphthyl)-propionic acid was 90%;

1-(4'-isobutyl-phenyl)-propanone (reaction time: 17 hours; reaction temperature: 60° C.), the yield of 2-(4'-isobutylphenyl)-propionic acid was 28%; m.p. 76° C.;

propionylphenyl (reaction time: 28 hours; reaction temperature: 70° C.), the yield of 2-phenyl-propionic acid was 32%;

1-(3'-phenoxy-phenyl)-propanone (reaction time: 32 hours; reaction temperature: 70° C.), the yield of α-dl-2-(3-phenoxy-phenyl)-propionic acid was 30%.

Similarly but adding slowly 1.05 moles of iodine for each mole of ketone and without adding the oxidant 2-propionylthiophen yielded 70% of 2-(2-thienyl)-propionic acid; and 1-(4'-isobutyl-phenyl)-propanone yielded 53% of 2-(4'-isobutylphenyl)-propionic acid.

EXAMPLE 3

Iodine (28 g; 0.11 mole) was added to a solution of 1-(6'-methoxy-2'-naphthyl)-propanone (21.4 g; 0.1 mole) in triethylorthoformate (120 ml; 0.72 mole) at room temperature. The mixture was stirred for 4 hours and then heated to reflux (67° C.) for 24 hours. The low boiling compounds were distilled up to 85° C. The mixture was cooled to 50° C. and anhydrous sodium sulfite (1 g) and deionized water (2 ml) were added. The mixture was stirred at the same temperature for 15 minutes and then sodium hydroxide (4.4 g; 0.11 mole) was added. The mixture was refluxed for 1 hour, diluted with water (500 ml), and acidified with 37% hydrochloric acid to pH 1. The precipitate was filtered, washed with water to neutrality and dried at 70° C. for 12 hours under reduced pressure.

18.4 g (titer 98%) of the desired product were obtained in this manner; yield, 79%.

Similar results were obtained by working in a similar manner but substituting the triethylorthoformate with C(OCH₃)₄; Yield, 87%;

triisopropylorthoformate and isopropyl alcohol; Yield, 81%.

We claim:

1. A process for preparing an arylalkanoic acid of the formula

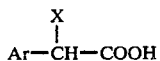

wherein X is H or methyl, and Ar is optionally-substituted homocyclic or heterocyclic aryl; which comprises adding iodine to a mixture of an arylalkanone of the formula

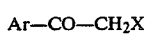

wherein Ar and X have the meanings indicated above, and an excess of an orthoester, heating of the reaction mixture, adding an inorganic base and finally an acid.

2. A process for preparing an arylalkanoic acid of formula

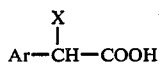

wherein X is H or methyl, and Ar is 6-methoxy-2-naphthyl, 2-thienyl, 4-isobutylphenyl, or 3-phenoxy-phenyl; which comprises adding iodine to a mixture of an arylalkanone of the formula

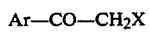

wherein Ar and X have the meanings indicated above, and an excess of an orthoester, heating of the reaction mixture, adding an inorganic base and finally an acid.

3. A process according to claim 2, in which 1 mole of an arylalkanone of formula (I) is reacted with 0.5–1.5 mole of iodine and at least 2 mole of an orthoester.

4. A process according to claim 2, further comprising the addition of an oxidant.

5. A process according to claim 2, further comprising the addition of an inert diluent.

6. A process according to claim 2, further comprising the addition of a solvent.

7. A process according to claim 2, further comprising the addition of a catalytic quantity of a protic acid.

8. A process according to claim 4, in which the oxidant is hydrogen peroxide, an organic peroxide, a perester, a peracid, or a hydroperoxide.

9. A process according to claim 8, in which the organic peroxide is a diacylperoxide.

10. A process according to claim 9, in which the diacylperoxide is dibenzoyl or dodecanoylperoxide.

11. A process according to claim 8, in which the perester is di-tert-butyl-peracetate, tert-cyclohexylpercarbonate, tert-butylperbenzoate, di-tert-butylperoxalate, or di-tert-butyl-perisobutyrrate.

12. A process according to claim 8, in which the peracid is m-chloroperbenzoic, or permaleic acid.

13. A process according to claim 8, in which the hydroperoxide is tert-butylhydroperoxide, or cumylhydroperoxide.

14. A process according to claim 5, in which the inert diluent is an aromatic hydrocarbon.

15. A process according to claim 14, in which the aromatic hydrocarbon is benzene, toluene, xylene, or nitrobenzene.

16. A process according to claim 2, in which the orthoester is an alkylorthoformate, an alkylorthoacetate, or an alkylorthocarbonate where the alkyl radical has from 1 to 4 carbon atoms.

* * * * *